(12) United States Patent
Patoiseau et al.

(10) Patent No.: US 6,191,130 B1
(45) Date of Patent: Feb. 20, 2001

(54) CYCLOHEXANE DERIVATIVES DIFUNCTIONALISED IN 1,4 AS LIGANDS OF 5T H1A RECEPTORS

(75) Inventors: Jean-François Patoiseau; Elisabeth Dupont-Passelaigue, both of Castres; Wouter Koek, Viviers-les-Montagnes, all of (FR)

(73) Assignee: Pierre Fabre Medicament, Boulogne (FR)

( * ) Notice: Under 35 U.S.C. 154(b), the term of this patent shall be extended for 0 days.

(21) Appl. No.: 09/529,783

(22) PCT Filed: Oct. 14, 1998

(86) PCT No.: PCT/FR98/02207

§ 371 Date: Apr. 14, 2000

§ 102(e) Date: Apr. 14, 2000

(87) PCT Pub. No.: WO99/20613

PCT Pub. Date: Apr. 29, 1999

(30) Foreign Application Priority Data

Oct. 16, 1997 (FR) .................................................. 97 12954

(51) Int. Cl.[7] .......................... C07D 253/06; A61K 31/53
(52) U.S. Cl. ............................................. 514/242; 544/182
(58) Field of Search ............................................. 544/182

(56) References Cited

FOREIGN PATENT DOCUMENTS

WO9501965A 1/1995 (WO).
WO9616949A 6/1996 (WO).

Primary Examiner—John M. Ford
(74) Attorney, Agent, or Firm—The Firm of Hueschen and Sage

(57) ABSTRACT

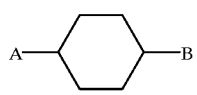

(I)

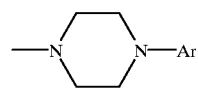

(IIa)

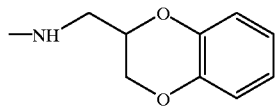

(IIb)

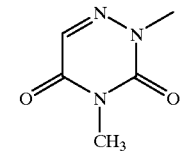

(IIIa)

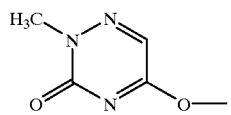

(IIIb)

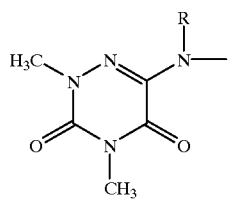

(IIIc)

The invention concerns novel cyclohexane derivatives difunctionalised in 1.4 of general formula (1) in which A represents a group such as (IIa) in which Ar itself represents an aromatic structure such as phenyl or pyrimidinyl optionally substituted by one or several groups such as $C_1$–$C_3$ alkyl, $C_1$–$C_3$ alkoxy, trifluoromethyl or halogen (IIb); B represents a heterocyclic group such as: 3,5-dioxo-(2H,4H)-1,2,4 triazine substituted in position 2 (IIIa); 3-oxo-(2H)-1,2,4 triazine substituted in position 5 (IIIb); 3,5-dioxo-6-amino-(2H,4H)-1,2,4-triazine (IIIc) in which R represents a $C_1$–$C_3$ alkyl group. The invention also concerns the salts of compounds of general formula I with pharmaceutically acceptable acids. It also concerns the various "cis" and "trans" isomers and the various enantiomers with asymmetric carbons.

6 Claims, No Drawings

CYCLOHEXANE DERIVATIVES DIFUNCTIONALISED IN 1,4 AS LIGANDS OF 5T H1A RECEPTORS

A subject-matter of the present invention is novel 1,4-functionalized cyclohexane derivatives, their preparation and their application in human therapeutics.

5-$HT_{1A}$ receptors have been claimed for their role in various pathologies, such as hypertension, sexual disfunctioning, anorexia and memory. The main target suggesting the involvement of 5-$HT_{1A}$ receptors is, however, disorders of the central nervous system, such as anxiety and depression. The hypotheses, supported by tests on animal models and clinical studies, suggest that more effective treatments of these pathologies can be envisaged with 5-$H_{1A}$ agonist compounds of high affinity which are very selective and highly effective.

3,5-Dioxo- (2H,4H)-1,2,4-triazine derivatives and 3,5-dioxo-6-amino-(2H,4H)-1,2,4-triazine derivatives have been claimed previously by the Applicant Company (FR 2,707,294 of Jun. 7, 1993 and FR 2,727,682 of Feb. 12, 1994).

The compounds of the present invention are characterized by their powerful affinity with regard to the 5-$HT_{1A}$ receptor in combination with a high selectivity, in particular with regard to the $D_2$ and $\alpha_1$ receptors, and a high intrinsic activity.

The compounds of the invention correspond to the general formula I

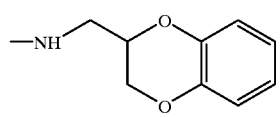

I in which

A represents a group of type

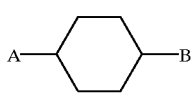

IIa in which Ar itself represents a structure of aromatic type, such as phenyl or pyrimidinyl, optionally substituted by one or more groups, such as $C_{1-3}$ alkyl, $C_1$–$C_3$ alkoxy, trifluoromethyl or halogen,

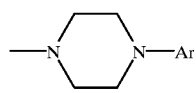

IIb

B represents a heterocyclic group of type
3,5-dioxo-(2H,4H)-1,2,4-triazine substituted at the 2-position, IIIa

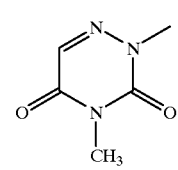

IIIa 3-oxo-(2H)-1,2,4-triazine substituted at the 5 position, IIIb

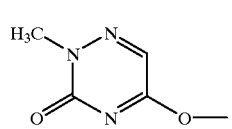

IIIb 3,5-dioxo-6-amino-(2H,4H)-1,2,4-triazine, IIIc

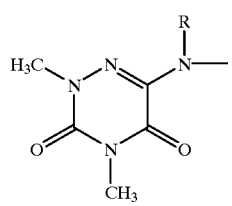

IIIc in which R represents a $C_1$–$C_3$ alkyl group.

The invention covers the salts of the compounds of general formula I with pharmaceutically acceptable acids. In addition, it covers the various "cis" and "trans" isomers and the various enantiomers of the compounds possessing asymmetric carbons.

SYNTHESIS

The compounds of the present invention can be synthesized by using the synthetic routes described hereinbelow or by using synthetic methods known to a person skilled in the art.

Method 1

The synthesis of the compounds of general formula I is characterized in that a derivative of general formula IV

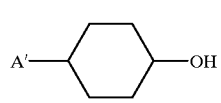

IV in which A' represents the IIa or IIb groups described above or IIc

IIc is condensed with an intermediate of type Va or Vb

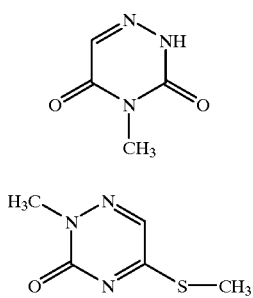

Va

Vb

The intermediate IV in which A'=IIc is advantageously used in the case of the coupling with the derivatives of type Va in order to give access to the compounds I in which A represents IIa with Ar representing an optionally substituted pyrimidinyl group. The compound from the condensation between the intermediates IV in which A'=IIc and Va is debenzylated by treating, for example, with α-chloroethyl chloroformate in methanol and by then condensing with optionally substituted 2-chloropyrimidine in the presence of a base, such as triethylamine in toluene.

The condensation between the derivatives IV and Va can be carried out according to the conditions of the Mitsunobu reaction.

The condensation between the derivatives IV and Vb can be carried out in the presence of a base, such as sodium hydride or potassium tert-butoxide in dioxane or THF.

Method 2

The synthesis of the compounds of general formula I according to Method 2 is characterized in that a derivative of general formula VI

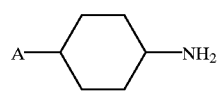

VI in which A has the same meaning as above, is treated with an intermediate of general formula Vc

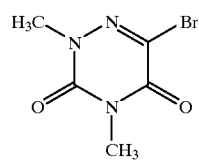

Vc

The condensation is carried out in the presence of a base, such as triethylamine in butanol.

The optional separation of the enantiomers of compounds obtained according to Method 1 or Method 2 which possess an asymmetric carbon is generally carried out on the final products by liquid chromatography on a chiral column.

Synthesis of the Alcohols IV a) When A' represents a group IIa or IIc

IIa

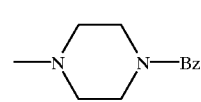

IIc the corresponding alcohols IVa or IVc

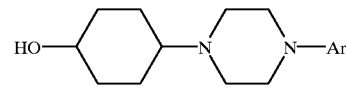

IVa

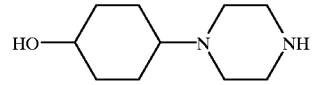

IVc can be obtained by condensing the piperazine VIIa or VIIb

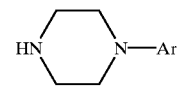

VIIa

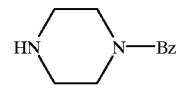

VIIb with cyclohexanedione monoethylene ketal in the presence of a reducing agent, such as NaBH(OAc)$_3$ in dichloromethane or NaBH$_3$CN in ethanol, to result in the intermediate VIIIa or VIIIb

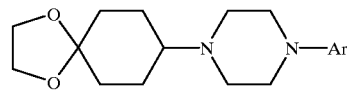

VIIIa

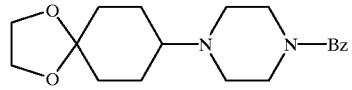

VIIIb which is hydrolyzed in an aqueous medium, such as hydrochloric acid, to give the ketone IXa or IXb

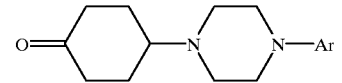

IXa

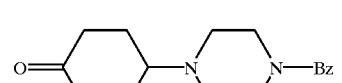

IXb

The ketone IXa is reduced to the alcohol IVa by reducing agents, such as NaBH$_4$ in ethanol, to give access predominantly to the "trans" alcohols IVa, or LS-selectride in THF, to result predominantly in the "cis" alcohols IVa.

The ketone IXb, reduced in a way analogous to that described above and then debenzylated by treating, for example, with α-chloroethyl chloroformate in methanol, provides the alcohol IVc. This alcohol, condensed with optionally substituted 2-chloro-pyrimidine in a solvent such as toluene, in the presence of a base, such as triethylamine, provides the alcohol IVa with Ar representing a group of pyrimidinyl type.

b) When A' represents a group IIb

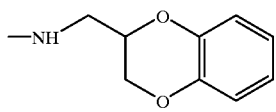
IIb the alcohol IVb can be obtained by condensing the amine X

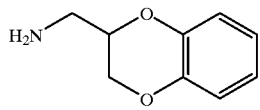
X with cyclohexanedione monoethylene ketal in the presence of a reducing agent, such as NaBH(OAc)$_3$ in dicholoromethane or NaBH$_3$CN in ethanol, to result in the intermediate VIIIc

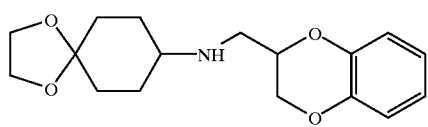
VIIIc which is hydrolyzed in aqueous hydrochloric acid medium to give the ketone IXc

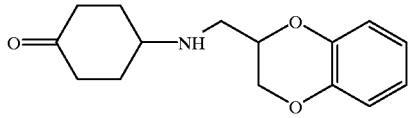
IXc

The ketone IXc is reduced to the alcohol IVb by reducing agents, such as NaBH$_4$ in ethanol, to give access predominantly to the "trans" compounds IVb, or LS-selectride in THF, to result predominantly in the "cis" alcohols IVb.

Synthesis of the Amines VI

The amines VI can be obtained from the corresponding ketones IX,

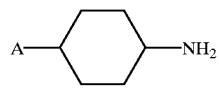
VI

IX

A having the same meaning as above, by treating them with hydroxylamine in an aqueous/alcoholic medium, to result in the imines XI

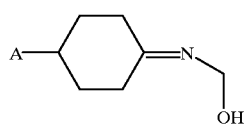
XI which are reduced by a hydride, such as LiAlH$_4$ in THF.

Synthesis of the Intermediates V

The compounds Va and Vc are synthesized according to the methods disclosed previously by the Applicant Company in Patents FR 2,727,682 of Feb. 12, 1994 and FR 2,707,294 of Jun. 7, 1993 respectively.

The compounds Vb can be obtained according to the process (Scheme 1) characterized by the following stages:

1-Condensation of glyoxylic acid with thiosemicarbazide, followed by a basic treatment, such as sodium hydroxide solution, 2-Methylation by methyl iodide in basic aqueous medium, followed by an acidic treatment, such as hydrochloric acid, 3-Sulfuration of the 5 position in the presence of Lawesson's reagent in a solvent such as pyridine, 4-Methylation by methyl iodide in basic aqueous medium, such as sodium hydroxide solution, 5-Methylation of the 2 position by methyl iodide in the presence of NaH in DMF.

Synthesis of the compounds V (Scheme 1)

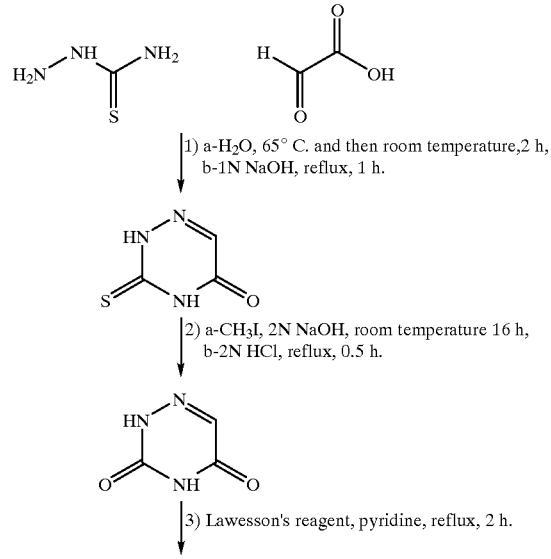

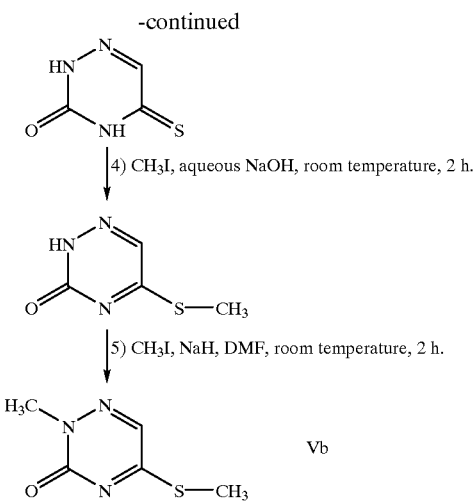

The following examples illustrate the invention without limiting the scope thereof.

The elemental analyses and the IR and NMR spectra confirm the structures of the compounds obtained according to the invention.

EXAMPLE 1

Cis-2-[4-[4-(3-Chlorophenyl)Piperazin-1-Yl]-Cyclohexyl]-4-Methyl-2H-[1,2,4]triazine-3,5-Dione Fumarate (1)

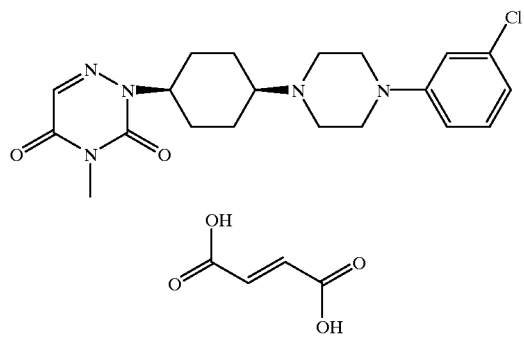

a) 2-Acetyl-2H-[1,2,4]triazine-3,5-dione (1a)

2H-[1,2,4]Triazin-3,5-dione (100 g, 884 mmol) is placed in 600 ml of acetic anhydride at reflux for 1.5 h. The reaction mixture is subsequently concentrated to dryness and the solid obtained is triturated in toluene. After filtering and rinsing with toluene, 130.5 g of beige crystals are isolated.

M.p.=148° C. TLC, 60 F 254 Merck silica gel $CH_2Cl_2$/MeOH: 90/10, Rf=0.68.

b) 4-Methyl-2H-[1,2,4]triazine-3,5-dione (1b)

NaH (60% in paraffin, 7 g, 175 mmol) is suspended in DMF under an inert atmosphere. The compound 1a (25 g, 161 mmol), diluted in 200 ml of DMF, is slowly run in dropwise. The reaction mixture is stirred for 1 h at room temperature and then $CH_3I$ (15 ml, 241 mmol) is added. This mixture is stirred for 3 h at room temperature.

After concentrating the reaction mixture to dryness, the residue obtained is taken up in 190 ml of ethanol, to which is added 1.5 g of para-toluenesulfonic acid. This mixture is refluxed for 5 h and then the solvent is evaporated under vacuum.

The oil obtained is taken up in $H_2O$ and then extracted with dichloromethane. The organic phases are dried over $MgSO_4$ and then concentrated. The precipitate which forms is filtered off and washed with ether. 10.5 g of yellow crystals are isolated.

M.p.=180° C. TLC, 60 F 254 Merck silica gel $CH_2Cl_2$/AcOEt: 70/30, Rf=0.46.

c) 1-(3-Chlorophenyl)-4-(1,4-dioxaspiro[4.5]dec-8-yl)-piperazine (1c)

Cyclohexanedione monoethylene ketal (18.3 g, 117.2 mmol) is placed in 45 ml of $Ti(OiPr)_4$ in the presence of 3-chlorophenylpiperazine (23 g, 117 mmol). This mixture is stirred for 2 h at room temperature and then 110 ml of absolute ethanol are added, followed by 6 g of $NaBH_3CN$. The reaction mixture is stirred for 20 h at room temperature.

After neutralizing using 24 ml of water, the titanium salts are removed by filtration. The filtrate is concentrated to dryness and the oil obtained is purified by silica flash chromatography (eluent $CH_2Cl_2$/AcOEt: 70/30). 29.6 g of oil (1c) are collected.

TLC, 60 F 254 Merck silica gel $CH_2Cl_2$/AcOEt: 70/30, Rf=0.18.

d) 4-[4-(3-Chlorophenyl)piperazin-1-yl]cyclohexanone (1d)

The compound 1c (29.6 g, 88 mmol) is placed in 195 ml of dioxane in the presence of 125 ml of a 6N hydrochloric acid solution and then the mixture is stirred for 22 h at room temperature.

The reaction mixture is neutralized with NaOH and then extracted with ethyl acetate. The organic phases are dried over $MgSO_4$ and then concentrated to dryness. The oil obtained (23.5 g) is used without further purification in the following stage.

TLC, 60 F 254 Merck silica gel $CH_2Cl_2$/MeOH: 95/5, Rf=0.36.

e) trans-4-[4-(3-Chlorophenyl)piperazin-1-yl]cyclohexanol (1e)

$LiAlH_4$ (3.4 g, 89.8 mmol) is suspended in 90 ml of THF under an inert atmosphere. The compound 1d, diluted in 41 ml of THF, is added dropwise and then the mixture is brought to reflux for 2 h.

After neutralizing using 13 ml of water, the reaction mixture is dried over $MgSO_4$. The inorganic materials are filtered off and the filtrate is concentrated to dryness. The residue obtained is purified by silica flash chromatography ($CH_2Cl_2$/MeOH: 90/10). 5.7 g of oil are collected.

TLC, 60 F 254 Merck silica gel $CH_2Cl_2$/MeOH: 90/10, Rf=0.28.

f) cis-2-[4-[4-(3-Chlorophenyl)piperazin-1-yl]cyclohexyl]-4-methyl-2H-[1,2,4]triazine-3,5-dione fumarate (1)

The alcohol 1e (0.96 g, 3.25 mmol) is placed, together with triphenylphosphine (0.86 g, 3.27 mmol) and compound 1b (0.46 g, 3.62 mmol), in 12 ml of THF under an inert atmosphere and cooled to 0° C. on a bed of ice. DEAD (0.51 ml, 3.23 mmol) is added dropwise and then the temperature of the reaction mixture is returned to room temperature. This mixture is stirred for 24 h at this temperature and then concentrated to dryness, and the residue obtained is purified by silica flash chromatography (eluent $CH_2Cl_2$/AcOEt: 70/30).

After salifying with fumaric acid in ethanol, 0.16 g of white solid is isolated.

M.p.=210° C. TLC, 60 F 254 Merck silica gel $CH_2Cl_2$/MeOH: 90/10, Rf=0.68.

EXAMPLE 2

Trans-2-[4-[(2,3-Dihydrobenzo[1,4]Dioxin-2-Ylmethyl)Amino]Cyclohexyl]-4-Methyl-2H-[1,2,4]Triazine-3,5-Dione Hemifumarate (2)

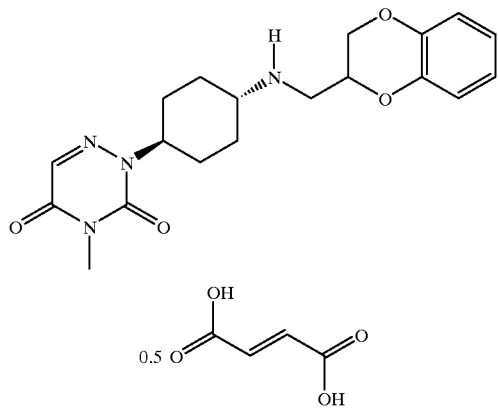

This compound is prepared according to the process described in Example 1 using, in Stage f, a cis and trans (30/70) mixture of 4-[(2,3-dihydrobenzo[1,4]dioxin-2-ylmethyl)amino]cyclohexanol (prepared according to the process described in Example 1 using $NaBH_4$ in EtOH in Stage e) and is then salified with fumaric acid in methanol.

M.p.=238° C. TLC, 60 F 254 Merck silica gel $CH_2Cl_2$/MeOH: 90/10, Rf=0.63.

EXAMPLE 3

Cis-4-Methyl-2-[4-(4-Pyrimidin-2-Yl-Piperazin-1-Yl)Cyclohexyl]-2H-[1,2,4]Triazine-3,5-Dione (3)

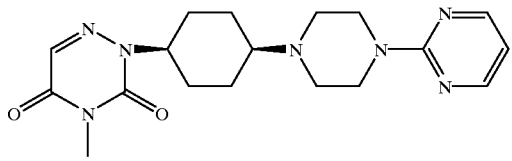

This compound is prepared according to the process described in Example 2 using a cis and trans (30/70) mixture of 4-(4-pyrimidin-2-yl-piperazin-1-yl)cyclohexanol (prepared according to the process described in Example 1 using $NaBH_4$ in EtOH in Stage e).

M.p.=166° C. TLC, 60 F 254 Merck silica gel $CH_2Cl_2$/MeOH: 90/10, Rf=0.46.

EXAMPLE 4

Trans-4-Methyl-2-[4-(4-Pyrimidin-2-Yl-Piperazin-1-Yl)Cyclohexyl]-2H-[1,2,4]Triazine-3,5-Dione (4)

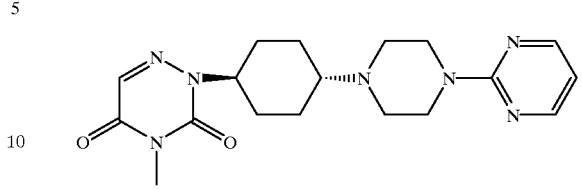

This compound is prepared according to the process described in Example 3.

M.p.=222° C. TLC, 60 F 254 Merck silica gel $CH_2Cl_2$/MeOH: 90/10, Rf=0.31.

EXAMPLE 5

Trans-4-Methyl-2-[4-[4-(4,6-Dimethylpyrimidin-2-Yl)Piperizin-1-Yl]Cyclohexyl]-2H-[1,2,4]Triazine-3,5-Dione (5)

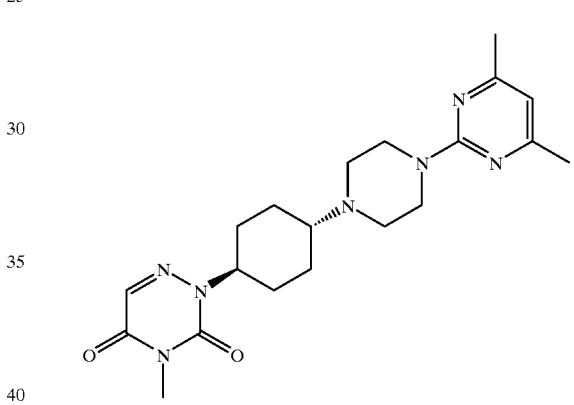

a) cis-4-[4-(4,6-Dimethylpyrimidin-2-yl)piperizin-1-yl]-cyclohexanol (5a)

LS-selectride (1M solution in THF, 22.6 ml, 22.6 mmol) is placed at −78° C. under an inert atmosphere.

4-[4-(4,6-Dimethylpyrimidin-2-yl)piperizin-1-yl]cyclohexanone (prepared according to Example 1 from (4,6-dimethyl-2-piperazin-1-yl)pyrimidine) (5.9 g, 20.4 mmol), diluted in 25 ml of THF at 0° C., is run in dropwise. This mixture is stirred for 2 h at −78° C. and then the temperature is brought to room temperature.

The reaction mixture is hydrolyzed with $H_2O$ and then extracted with dichloromethane. The organic phases are dried over magnesium sulfate and the concentrated to dryness. The residue isolated is purified by silica flash chromatography (eluent $CH_2Cl_2$/MeOH/$NH_4OH$: 90/9/1). 3.8 g of alcohol 5a are isolated.

TLC, 60 F 254 Merck silica gel $CH_2Cl_2$/MeOH: 90/9/1, Rf=0.50.

b) trans-4-Methyl-2-[4-[4-(4,6-dimethylpyrimidin-2-yl)piperizin-1-yl]cyclohexyl]-2H-[1,2,4]triazine-3,5-dione (5)

This compound is prepared according to the process described in Example 1 using, in Stage f, the alcohol 5a.

M.p.=255° C. TLC, 60 F 254 Merck silica gel $CH_2Cl_2$/MeOH/$NH_4OH$: 90/9/1, Rf=0.60.

EXAMPLE 6

Trans-4-Methyl-2-[4-[4-(4-Methylpyrimidin-2-Yl)Piperazin-1-Yl]Cyclohexyl]-2H-[1,2,4]triazine-3,5-dione (6)

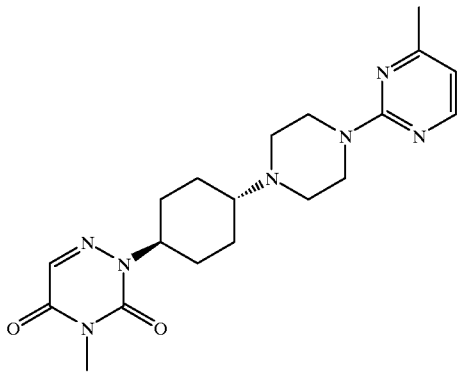

This compound is prepared according to the process described in Example 1 using, in Stage f, cis-4-[4-(4-methylpyrimidin-2-yl)piperazin-1-yl]cyclohexanol (prepared according to the process described in Example 5 in Stage a).

M.p.=210° C. TLC, 60 F 254 Merck silica gel $CH_2Cl_2$/MeOH: 90/10, Rf=0.41.

EXAMPLE 7

Trans-2-[4-[4-(4-Chloropyrimidin-2-Yl)-piperazin-1-Yl]Cyclohexyl]-4-Methyl-2H-[1,2,4]Triazine-3,5-dione (7)

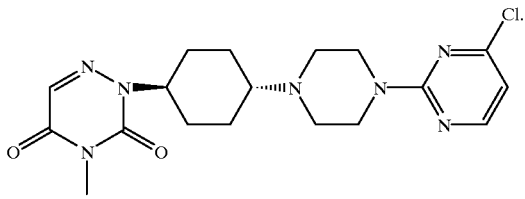

a) cis-4-Piperizin-1-yl-cyclohexanol (7a)

cis-4-(4-Benzylpiperizin-1-yl)cyclohexanol (prepared according to the process described in Example 5 using 4-(4-benzylpiperizin-1-yl)cyclohexanone in Stage a) (11.6 g, 30.3 mmol) is placed in 80 ml of dichloromethane at 0° C. α-Chloroethyl chloroformate (9.9 ml, 90.9 mmol) is run in dropwise and the mixture is stirred for 0.5 h at 0° C.

The reaction mixture is concentrated to dryness and then taken up in 80 ml of methanol. After having refluxed this mixture for 45 min, the solution is concentrated to dryness. The residue obtained is taken up in $H_2O$ (pH=11) and extracted with dichloromethane. The organic phases are dried ($MgSO_4$) and then concentrated to dryness. After purifying by silica flash chromatography (eluent $CH_2Cl_2$/MeOH/$NH_4OH$: 80/18/2) and then recrytallizing from ether, 1.7 g of brown solid are isolated.

TLC, 60 F 254 Merck silica gel $CH_2Cl_2$/MeOH/$NH_4OH$: 80/18/2, Rf=0.30.

b) trans-2-[4-[4-(4-Chloropyrimidin-2-yl)piperazin-1-yl]cyclohexyl]-4-methyl-2H-[1,2,4]triazine-3,5-dione (7)

The compound 7a (1.5 g, 5.1 mmol) is placed in 40 ml of toluene in the presence of 2,4-dichloropyrimidine (0.84 g, 5.6 mmol) and of triethylamine (0.78 ml, 5.6 mmol).

After having heated this mixture at reflux for 1.5 h, the solvent is evaporated under vacuum. The residue is taken up in $H_2O$ and then extracted with $CH_2Cl_2$. After drying the organic phases ($MgSO_4$) and concentrating to dryness, the light-colored oil obtained is purified by silica flash chromatography (eluent $CH_2Cl_2$/MeOH: 95/5). 0.4 g of white solid is isolated.

M.p.=201° C. TLC, 60 F 254 Merck silica gel $CH_2Cl_2$/MeOH: 95/5, Rf=0.22.

EXAMPLE 8

Trans-2-[4-[4-(5-Fluoropyrimidin-2-Yl)Piperazin-1-Yl]Cyclohexyl]-4-methyl-2H-[1,2,4]Triazine-3,5-dione (8)

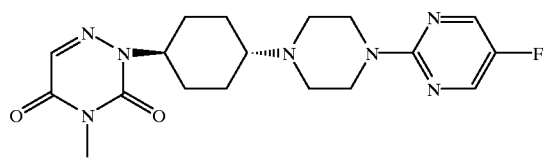

This compound is prepared according to Example 7 using, in Stage b, 2-chloro-5-fluoro-pyrimidine.

M.p. =220° C. TLC, 60 F 254 Merck silica gel $CH_2Cl_2$/MeOH: 90/10, Rf=0.35.

EXAMPLE 9

Trans-2-Methyl-5-[4-(4-pyrimidin-2-Yl-Piperizin-1-Yl)Cyclohexyloxy]-2H-[1,2,4]triazin-3-one (9)

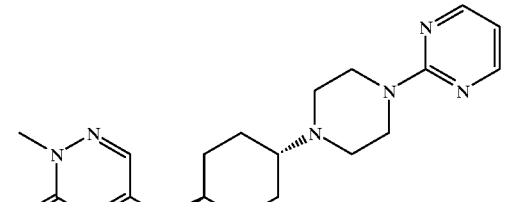

a) 5-Thioxo-4,5-dihydro-2H-[1,2,4]triazin-3-one (9a)

98.3 g (243 mmol) of Lawesson's reagent are added to a solution of 2H-[1,2,4]triazin-3,5-dione (50 g, 442 mmol) in 400 ml of pyridine. The mixture is brought to reflux for 4 h. After evaporating the solvent under reduced pressure, the residue obtained is taken up in 400 ml of water. The brown precipitate which forms is isolated by filtration. These crystals are taken up in $H_2O$ and extracted with ethyl acetate. After drying the organic phases ($MgSO_4$) and concentrating them to dryness, yellow crystals are obtained.

Retreatment of the water (400 ml) by extraction with ethyl acetate makes it possible to isolate a fresh solid fraction. In total, after drying, 60 g of yellow crystals are obtained.

M.p.=239° C. TLC, 60 F 254 Merck silica gel $CH_2Cl_2$/MeOH: 90/10, Rf=0.4.

b) 5-Methylsulfanyl-2H-[1,2,4]triazin-3-one (9b)

The compound 9a (30 g, 232 mmol) and $CH_3I$ (15.9 ml, 255 mmol) are placed in 300 ml of water. 18.6 g of NaOH (465 mmol) are added and the mixture is stirred for 1 h at room temperature. The reaction mixture, cooled on a bed of ice, is neutralized using 27 ml of acetic acid and then extracted with dichloromethane. The organic phases are dried ($MgSO_4$) and then concentrated to dryness. After recrystallizing from ether, 29.9 g of compound 9b are isolated.

M.p.=171° C. TLC, 60 F 254 Merck silica gel CH$_2$Cl$_2$/MeOH: 90/10, Rf=0.5.

c) 2-Methyl-5-methylsulfanyl-2H-[1,2,4]triazin-3-one (9c)

A suspension, placed under nitrogen, of NaH (60% in liquid paraffin, 4.4 g, 110 mmol) in 50 ml of DMF is cooled to 0° C. on a bed of ice. The compound 9b (15.9 g, 111 mmol), diluted in 100 ml of DMF, is run into the suspension dropwise. The mixture is subsequently stirred for 1 h at room temperature.

After concentrating the reaction mixture to dryness, the residue is taken up in H$_2$O and extracted with CH$_2$Cl$_2$. The organic phases are dried over MgSO$_4$ and then evaporated under reduced pressure.

After crystallizing from EtOH/isopropyl ether and then drying, 13.9 g of product 9c are isolated in the form of beige crystals.

M.p.=106° C. TLC, 60 F 254 Merck silica gel CH$_2$Cl$_2$/MeOH: 95/5, Rf=0.52.

d) trans-2-Methyl-5-[4-(4-pyrimidin-2-yl-piperizin-1-yl)cyclohexyloxy]-2H-[1,2,4]triazin-3-one (9)

NaH (60% in paraffin, 0.56 g, 14 mmol) is suspended in 20 ml of dioxane under an inert atmosphere at 0° C.

trans-4-(4-Pyrimidin-2-yl-piperazin-1-yl)cyclohexanol (prepared according to the process described in Example 1 using, in Stage e, NaBH$_4$ in ethanol) (4.0 g, 15.4 mmol), diluted in 20 ml of dioxane, is then added. The mixture is stirred while the temperature rises to room temperature.

After having placed the reaction mixture back on the bed of ice, the compound 9c (2.2 g, 14 mmol), diluted in 15 ml of dioxane, is added and the reaction mixture is stirred for 1 h at 0° C.

After concentrating to dryness, the residue obtained is taken up in water and then extracted with dichloromethane. The organic phases are dried over MgSO$_4$ and then concentrated to dryness. The oil isolated is purified by silica flash chromatography (eluent CH$_2$Cl$_2$/MeOH/NH$_4$OH: 90/9/1). After recrystallizing from methanol, 2 g of white precipitate are isolated.

M.p.=200° C. TLC, 60 F 254 Merck silica gel CH$_2$Cl$_2$/MeOH/NH4OH: 90/9/1, Rf=0.35.

EXAMPLE 10

Trans-2-Methyl-5-[4-[4-(4-Methylpyrimidin-2Yl)Piperazin-1-yl]Cyclohexyloxy]-2H-[1,2,4]Triazin-3-one (10)

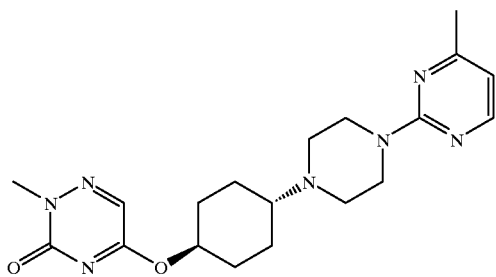

a) trans-4-Piperazin-1-yl-cyclohexanol (10a)

trans-4-(4-Benzylpiperazin-1-yl)cyclohexanol (prepared from benzylpiperazine according to the process described in Example 1 using, in Stage e, NaBH$_4$ in ethanol) (15 g, 54.6 mmol) is placed in 150 ml of ethanol under 4 bar of hydrogen in the presence of 10% palladium-on-charcoal (1 g). After stirring for 72 h, the catalyst is filtered off on celite and the filtrate is concentrated to dryness. 9.6 g of light-colored oil are isolated.

TLC, 60 F 254 Merck silica gel CH$_2$Cl$_2$/MeOH/NH$_4$OH: 80/18/2, Rf=0.42.

b) trans-4-[4-(4-Methylpyrimidin-2-yl)piperazin-1-yl]cyclohexanol (10b)

The compound 10a (4.3 g, 23.3 mmol) is placed in 100 ml of toluene in the presence of 2-chloro-4-methylpyrimidine (3 g, 23.3 mmol) and of triethylamine (4.9 ml, 35.1 mmol) and then this mixture is heated at reflux for 16 h.

After evaporating the solvent under vacuum, the residue and taken up in basic H$_2$O (pH=11) and extracted with dichloromethane. The organic phases are dried (MgSO$_4$) and then concentrated to dryness. The residue isolated is purified by silica flash chromatography (eluent CH$_2$Cl$_2$/MeOH/NH$_4$OH: 80/18/2) and 4 g of compound 10b are isolated.

TLC, 60 F 254 Merck silica gel CH$_2$Cl$_2$/MeOH/NH$_4$OH: 80/18/2, Rf=0.77.

c) trans-2-Methyl-5-[4-[4-(4-methylpyrimidin-2-yl)piperazin-1-yl]cyclohexyloxy]-2H-[1,2,4]triazin-3-one (10)

This compound is prepared according to the process described in Example 9 using the intermediate 10b in Stage d.

M.p.=189° C. TLC, 60 F 254 Merck silica gel CH$_2$Cl$_2$/MeOH: 90/10, Rf=0.44.

EXAMPLE 11

Trans-2-Methyl-5-[4-[4-(4,6-Dimethyl-Pyrimidin-2-Yl)Piperazin-1-Yl]Cyclohexyloxy]-2H-[1,2,4]triazin-3-one (11)

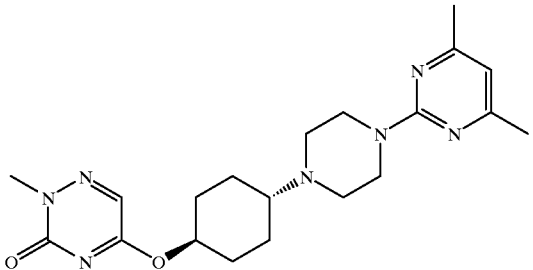

This compound is prepared according to the process described in Example 10 using 2-chloro-4,6-dimethylpyrimidine in Stage b.

M.p.=211° C. TLC, 60 F 254 Merck silica gel CH$_2$Cl$_2$/MeOH: 90/10, Rf=0.54.

EXAMPLE 12

Trans-2-Methyl-5-[4-[4-(4-Chloropyrimidin-2-Yl)Piperazin-1-Yl]Cyclohexyloxy]-2H-[1,2,4]Triazin-3-One (12)

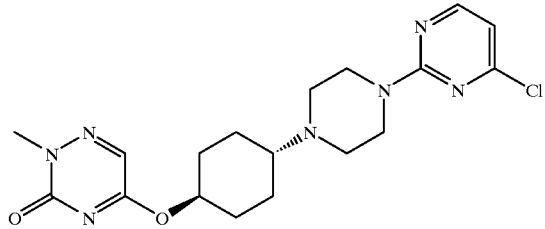

This compound is prepared according to the process described in Example 10 using 2,4-dichloropyrimidine in Stage b.

M.p.=214° C. TLC, 60 F 254 Merck silica gel CH₂Cl₂/MeOH: 90/10, Rf=0.57.

EXAMPLE 13

Trans-2-Methyl-5-[4-[4-(4-Methoxypyrimidin-2-Yl)Piperazin-1-yl]Cyclohexyloxy]-2H-[1,2,4]triazin-3-One (13)

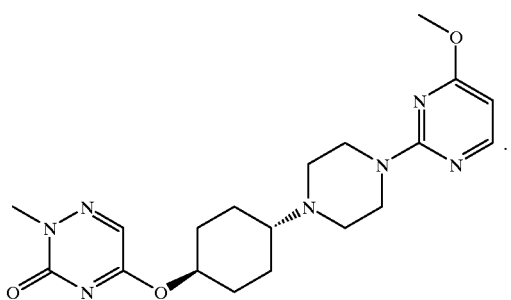

This compound is prepared according to the process described in Example 10 using 2-chloro-4-methoxypyrimidine in Stage b.

M.p.=196° C. TLC, 60 F 254 Merck silica gel CH₂Cl₂/MeOH: 90/10, Rf=0.43.

EXAMPLE 14

Trans-2-Methyl-5-[4-[4-(4-Trifluoro-Methylpyrimidin-2-Yl)Piperazin-1-Yl]Cyclohexyloxy]-2H-[1,2,4]Triazin-3-One (14)

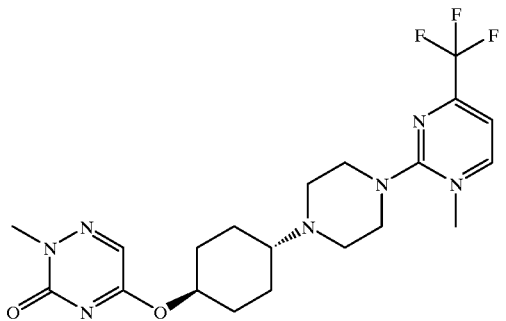

This compound is prepared according to the process described in Example 10 using 2-chloro-3-(trifluoromethyl)pyrimidine in Stage b.

M.p.=184° C. TLC, 60 F 254 Merck silica gel CH₂Cl₂/MeOH: 90/10, Rf=0.73.

EXAMPLE 15

Trans-2-Methyl-5-[4-[4-(5-Fluoropyrimidin-2-Yl)Piperazin-1-yl]Cyclohexyloxy]-2H-[1,2,4]Triazin-3-One (15)

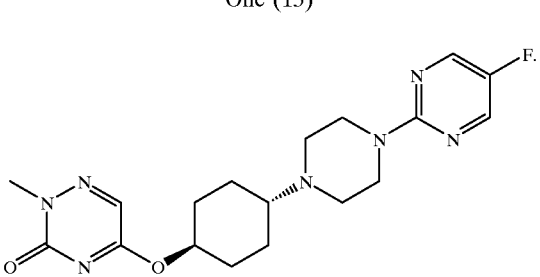

This compound is prepared according to the process described in Example 10 using 2-chloro-5-fluoropyrimidine in Stage b.

M.p.=209° C. TLC, 60 F 254 Merck silica gel CH₂Cl₂/MeOH: 90/10, Rf=0.61.

EXAMPLE 16

Trans-5-[4-[(2,3-Dihydrobenzo[1,4]Dioxin-2-Ylmethyl)Amino]Cyclohexyloxy]-2-Methyl-2H-[1,2,4]Triazin-3-One (16)

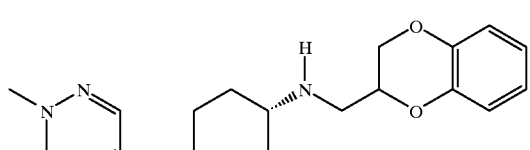

This compound is prepared according to the process described in Example 9 using trans-4-[(2,3-dihydrobenzo[1,4]dioxin-2-ylmethyl)amino]cyclohexanol (prepared according to the process described in Example 1 using, in Stage e, NaBH₄ in ethanol) in Stage d.

M.p.=114° C. TLC, 60 F 254 Merck silica gel CH₂Cl₂/MeOH: 90/10, Rf=0.61.

EXAMPLE 17

Trans-6-{4-[4-(3-Chlorophenyl)Piperazin-1-Yl]Cyclohexylamino}-2,4-Dimethyl-2H-[1,2,4]Triazine-3,5-Dione (17)

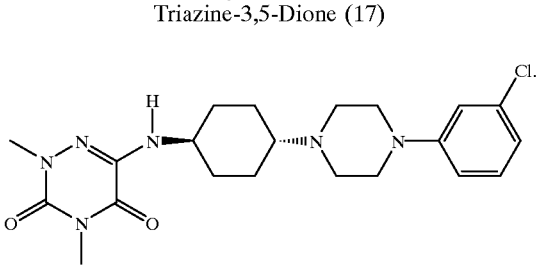

a) 2,4-Dimethyl-2H-[1,2,4]triazine-3,5-dione (17a)

NaH (60% in paraffin, 8.8 g, 220 mmol) is suspended in 100 ml of DMF under an inert atmosphere. A solution of 2H-[1,2,4]triazine-3,5-dione (25 g, 220 mmol) is added dropwise and then this mixture is stirred for 0.5 h at room temperature. CH₃I (27.4 ml, 440 mmol) is added and then stirring is continued overnight.

The solvent is concentrated to dryness under vacuum and then the residue is taken up in 300 ml of DMF, to which are added, under an inert atmosphere, 8.8 g of NaH (60% in paraffin, 220 mmol).

After stirring for 4 h, CH$_3$I is added (27.4 ml, 440 mmol) and the mixture is stirred overnight at room temperature.

The reaction mixture is concentrated to dryness under vacuum and the residue isolated is taken up in a saturated aqueous NaCl solution and extracted with ethyl acetate. The organic phases are dried over Na$_2$SO$_4$ and then evaporated under vacuum. After crystallizing and washing with water, 16.4 g of compound 17a are obtained.

M.p.=64° C. TLC, 60 F 254 Merck silica gel CH$_2$Cl$_2$/AcOEt: 70/30, Rf=0.53.

b) 6-Bromo-2,4-dimethyl-2H-[1,2,4]triazine-3,5-dione (17b)

The compound 17a (13.3 g, 94.1 mmol) is placed in 100 ml of water in the presence of bromine (18 ml, 351 mmol) and then this mixture is heated at 60° C. for 12 h.

After concentrating to dryness, the residue obtained is taken up in H$_2$O and then extracted with ethyl acetate. The organic phases are dried over MgSO$_4$ and then evaporated under vacuum. After recrystallizing from ether, 7.8 g of compound 17b are isolated.

M.p.=104° C. TLC, 60 F 254 Merck silica gel CH$_2$Cl$_2$/AcOEt: 70/30, Rf=0.73.

c) 4-[4-(3-Chlorophenyl)piperazin-1-yl]cyclohexanone oxime (17c)

The compound 1d (15.3 g, 52.3 mmol) is placed in a mixture of 143 ml of EtOH and 7 ml of water in the presence of hydroxylamine hydrochloride (5.9 g, 83.7 mmol) and of sodium hydroxide (14.5 g, 130.7 mmol).

The mixture is stirred for 1 h at room temperature and then 70 ml of water are added. The reaction mixture is extracted with ethyl acetate.

The organic phases are dried over MgSO$_4$ and then concentrated to dryness. 15.3 g of orange solid are isolated, which product is used without further purification in the following stage.

TLC, 60 F 254 Merck silica gel CH$_2$Cl$_2$/MeOH: 95/5, Rf=0.12.

d) cis- and trans-4-[4-(3-Chlorophenyl)piperazin-1-yl]cyclohexylamine (17d)

LiAlH$_4$ (8.4 g, 221 mmol) is suspended in 219 ml of THF under an inert atmosphere. The compound 17c (20.8 g, 67.6 mmol), diluted in 227 ml of THF, is added dropwise and then the mixture is brought to reflux for 2 h.

The reaction mixture is neutralized using 32 ml of water and is then dried with MgSO$_4$. After filtering through sintered glass, the filtrate is concentrated to dryness. The orange oil isolated is purified by silica flash chromatography (eluent CH$_2$Cl$_2$/MeOH/NH$_4$OH: 80/18/2). 3.4 g of cis compound 17d and 3.7 g of trans compound 17d are recovered.

TLC, 60 F 254 Merck silica gel CH$_2$Cl$_2$/MeOH/NH$_4$OH: 80/18/2, Rf$_{cis}$=0.43, Rf$_{trans}$=0.31.

e) trans-6-{4-[4-(3-Chlorophenyl)piperazin-1-yl]cyclohexylamino}-2,4-dimethyl-2H-[1,2,4]triazine-3,5-dione (17)

The trans compound 17d (3.7 g, 12.4 mmol) is placed in 45 ml of n-BuOH and triethylamine (3.6 ml, 25.8 mmol) in the presence of the intermediate 17b. This mixture is brought to reflux for 36 h and then the solvent is concentrated to dryness under vacuum. The brown residue obtained is taken up in H$_2$O and extracted with ethyl acetate. The organic phases are dried over MgSO$_4$ and then evaporated under vacuum. After purifying by silica flash chromatography (eluent CH$_2$Cl$_2$/MeOH: 95/5) and decoloring with animal charcoal in ethanol, a white precipitate is isolated (0.5 g).

M.p.=178° C. TLC, 60 F 254 Merck silica gel CH$_2$Cl$_2$/MeOH: 90/10, Rf=0.67.

EXAMPLE 18

Cis-6-{4-[4-(3-Chlorophenyl)Piperazin-1-Yl]Cyclohexylamino}-2,4-Dimethyl-2H-[1,2,4]Triazine-3,5-Dione (18)

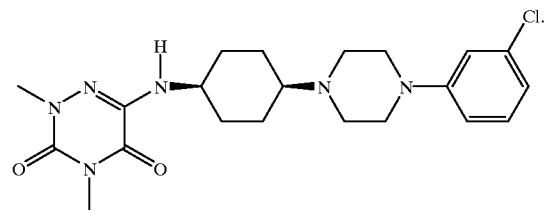

This compound is prepared according to the process described in Example 17 using, in Stage e, the cis intermediate 17d.

EXAMPLE 19

Trans-6-({4-[4-(3-Chlorophenyl)Piperazin-1-Yl]Cyclohexyl}Methylamino)-2,4-Dimethyl-2H-[1,2,4]Triazine-3,5-Dione (19)

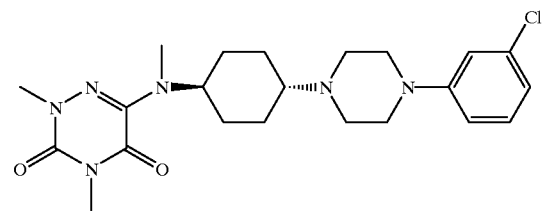

The compound 17 (0.5 g, 1.2 mmol) is placed in 14 ml of THF under an inert atmosphere in the presence of NaBH$_4$ (0.2 g, 5.3 mmol) and of paraformaldehyde (0.3 g, 11.3 mmol). Trifluoroacetic acid (7 ml, 90.8 mmol) is added dropwise and then this mixture is stirred for 20 h at room temperature.

The reaction mixture is added to a solution comprising 19 ml of 25% NaOH and 19 ml of saturated aqueous NaCl solution.

After extract with dichloromethane, the organic phases are dried over MgSO$_4$ and then concentrated to dryness. The residue obtained is purified by silica flash chromatography (eluent CH$_2$Cl$_2$/MeOH: 95/5). After crystallizing from ethanol, 0.4 g of white solid is isolated.

M.p.=179° C. TLC, 60 F 254 Merck silica gel CH$_2$Cl$_2$/MeOH: 95/5, Rf=0.38.

EXAMPLE 20

Cis-6-({4-[4-(3-Chlorophenyl)Piperazin-1-Yl]
Cyclohexyl}Methylamino)-2,4-Dimethyl-2H-[1,2,4]
Triazine-3,5-dione (20)

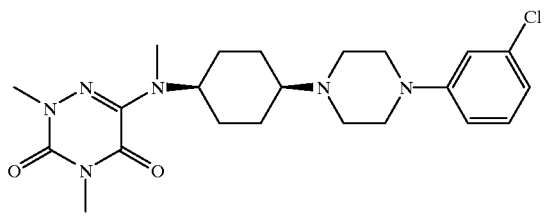

This compound is prepared from the intermediate 18 according to the process described in Example 19.

M.p.=124° C. TLC, 60 F 254 Merck silica gel CH$_2$Cl$_2$/MeOH: 95/5, Rf=0.58.

EXAMPLE 21

Trans-2,4-Dimethyl-6-[4-(4-Pyrimidin-2-Yl-
Piperazin-1-Yl)Cyclohexylamino]-2H-[1,2,4]
Triazine-3,5-Dione (21)

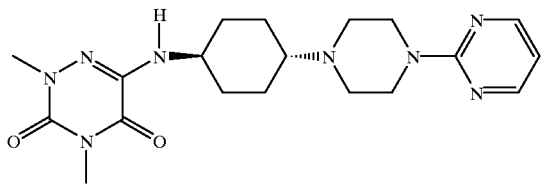

This compound is prepared according to the process described in Example 17 using trans-4-[4-pyrimidin-2-yl-piperazin-1-yl]cyclohexylamine in Stage e.

M.p.=173° C. TLC, 60 F 254 Merck silica gel CH$_2$Cl$_2$/MeOH: 90/10, Rf=0.46.

EXAMPLE 22

Cis-2,4-Dimethyl-6-[4-(4-Pyrimidin-2-Yl-Piperazin-
1-Yl)Cyclohexylamino]-2H-[1,2,4]Triazine-3,5-
dione (22)

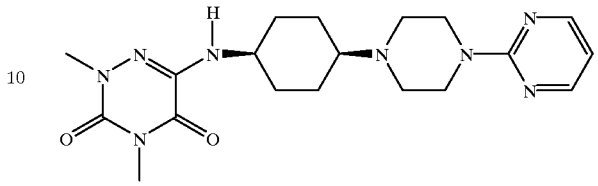

This compound is prepared according to the process described in Example 17 using cis-4-[4-pyrimidin-2-yl-piperazin-1-yl]cyclohexylamine in Stage e.

M.p.=170° C. TLC, 60 F 254 Merck silica gel CH$_2$Cl$_2$/MeOH: 90/10, Rf=0.47.

The compounds of the invention have been subjected to pharmacological tests which have demonstrated their advantage as therapeutically active substances.

Binding to the 5-HT$_{1A}$, D$_2$ dopaminergic and α1-adrenergic receptors:

Brains from male Sprague-Dawley 180–200 g rats [Ico: OFA SD (I.O.P.S. Caw); Iffa Credo, France], maintained at −70° C., were used in all the studies.

The affinity of the products for the various receptors was determined by displacement of radioactive ligands under the conditions summarized in Table 1.

The reaction is halted by rapid filtration, under vacuum, through Whatman GF/B filters and the tubes are rinsed with 2×5 ml of Tris-HCl 50 mM, pH 7.4, buffer at 25° C. The radioactivity collected on the filter is analyzed by liquid scintillation after addition of 4 ml of liquid scintillant (Emulsifier Safe, Packard). All the experiments are carried out in triplicate.

The inhibition constants (Ki) of the products are estimated from the displacement experimentations by using the EBDA (equilibrium binding data analysis) Radlig Version 4 non linear regression program (Biosoft, Cambridge, UK; McPherson, 1985).

The pKi (−log Ki) values are given in the form of the mean±SEM of at least 3 experimentations (Table 2).

TABLE 1

| | | | | | | | | | |
|---|---|---|---|---|---|---|---|---|---|
| | \[$^3$H\]ligand | | | | | Incubation | | Non specific binding | |
| Binding site | K$_D$ (nM) | Concentration (nM) | Tissue Type | Concentration | Time (min) | Temperature (° C.) | Product | Concentration (μM) | Buffer | References |
| 5-HT$_{1A}$ | 8-OH-DPAT (3.1) | 0.2 | cortex | 10 mg/ml | 30 | 23 | 5-HT | 10 | A | Assié and Koek, Eur. J. Pharmacol., 304, 15–21, 1996. |
| D$_2$ | YM-09151-2 (0.036) | 0.05 | striatum | 1 mg/ml | 60 | 23 | (+)-Buta clamol | 1 | B | Assié et al., Eur. J. Pharmacol., 237, 183–189, 1993. |
| α$_1$ | Prazosin (0.063) | 0.1 | cortex | 5 mg/ml | 30 | 23 | Phentolamine | 50 | C | Assié and Koek, Eur. J. Pharmacol., 304, 15–21, 1996. |

Buffers: (A) Tris HCl 50 mM pH 7.4, pargyline 10 μM, CaCl$_2$ 4 mM, 0.1% ascorbic acid; (B) Tris HCl 50 mM pH 7.4, NaCl 120 mM, KCl 5 mM; (C) Tris HCl 50 mM pH 7.4

TABLE 2

| Compound No. | pKi 5-HT$_{1A}$ | α$_1$ | D$_2$ |
|---|---|---|---|
| 4 | 8.43 | <5.0 | <5.0 |
| 5 | 9.22 | 5.89 | <5.0 |
| 6 | 9.09 | 6.10 | <5.0 |
| 9 | 9.15 | <5.0 | <5.0 |
| 10 | 9.60 | 5.95 | <5.0 |
| 11 | 9.60 | 5.72 | <5.0 |
| 12 | 9.54 | 6.21 | <5.0 |
| 13 | 9.28 | 6.65 | <5.0 |
| 16 | 9.78 | — | — |
| 17 | 9.40 | 7.74 | 6.22 |
| 19 | 9.71 | 7.86 | <5.0 |
| Buspirone | 7.65 | 6.19 | 7.49 |
| Flesinoxan | 8.91 | 6.50 | 7.05 |

Serotoninergic syndrome:

The central activity of the compounds of the invention was evaluated by their ability to provoke the 5-HT syndrome, which is characterized by:

- an alternating bending and stretching of the forepaws (reciprocal fore-paw treading: FPT)
- the retraction of the lower lip (lower lip retraction: LLR)
- a position or the ventral surface of the animal is in contact with the ground and the hind paws extended (flat body posture: FBP).

The experiments on the evaluation of the 5-HT syndrome are carried out with the male rat (Sprague-Dawley) according to the technique described by F. C. Colpaert et al. (Drug. Dev. Res., 26, 21–48, 1992) and M. S. Kleven et al. (J.P.E.T., 282, 747–759, 1997).

The active doses (ED$_{50}$) for some derivatives of the invention, in comparison with reference products such as Buspirone and Flesinoxan, are given in Table 3 by way of example.

TABLE 3

5-HT syndrome

| Compound No. | ED$_{50}$ mg/kg po | | |
|---|---|---|---|
| | FBP | LLR | FPT |
| 4 | 1.25 | 0.31 | 1.25 |
| 5 | 0.08 | <0.04 | 0.08 |
| 6 | 0.08 | 0.08 | 0.08 |
| 9 | 0.08 | 0.08 | 0.31 |
| 10 | 0.08 | 0.02 | 0.08 |
| 11 | 0.02 | 0.02 | 0.08 |
| 12 | 0.08 | 0.08 | 0.08 |
| 13 | 0.31 | 0.08 | 0.31 |
| 14 | 0.31 | 0.08 | 0.31 |
| 15 | 1.25 | 0.31 | >2.5 |
| 16 | 0.31 | 0.08 | >2.5 |
| Buspirone | 20 | 2.5 | >40 |
| Flesinoxan | 1.25 | 1.25 | 5 |

Antidepressant activity: Forced swimming test:

The compounds of the invention are tested according to the procedure described by R. Porsolt et al. (Eur. J. Pharmacol., 47, 379–391, 1978).

The active doses (ED$_{50}$) are calculated for each compound according to the percentage of animals exhibiting a significant decrease, in comparison with the control animals (p<0.05), in the immobility time (Table 4).

TABLE 4

| Compound No. | ED$_{50}$ mg/kg po |
|---|---|
| 4 | 1.25 |
| 5 | 0.31 |
| 9 | 0.31 |
| 10 | 0.08 |
| 11 | 0.08 |
| 12 | 0.74 |
| Buspirone | >160 |
| Flesinoxan | 1.25 |

The results of the various tests show that the compounds of general formula I possess, in vitro, a high affinity for the serotoninergic receptors of 5-HT$_{1A}$ type and good selectivity with regard to α$_1$ and D$_2$ receptors. They show, in vivo, an agonist activity with regard to 5-HT$_{1A}$ receptors and are powerfully active with regard to behavioral models, such as the forced swimming test.

The compounds of the invention can therefore be of use in the treatment of anxiety, depression, pain, neurodegeneration, schizophrenia, Alzheimer's disease and sleep disorders, for the regulation of food intake, for the regulation of gastric secretion and for the treatment of vascular, cardiovascular and cerebrovascular disorders, such as hypertension or migraine.

The pharmaceutical preparations comprising compounds of general formula I as active principle can be formulated for oral, rectal or parenteral administration, for example in the form of capsules, including hard gelatin capsules, tablets, granules, liquid solutions, syrups or suspensions to be taken orally, and can comprise the appropriate excipients.

It is also possible to combine therein other pharmaceutically and therapeutically acceptable active principles.

What is claimed is:

1. Difunctionalized cyclohexane derivatives selected from those of formula I

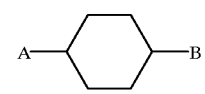

I in which

A represents a group of formula

IIa in which Ar represents a structure chosen from phenyl and pyrimidinyl, optionally substituted by one or more C$_{1-3}$ alkyl, C$_1$–C$_3$ alkoxy, trifluoromethyl, and halogen,

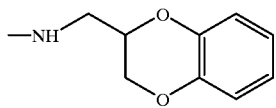

B represents a heterocyclic group selected from 3,5-dioxo-(2H,4H)-1,2,4-triazine substituted at the 2 position, (IIIa)

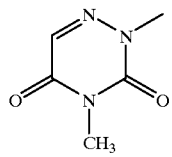

3-oxo-(2H)-1,2,4-triazine substituted at the 5 position, (IIIb)

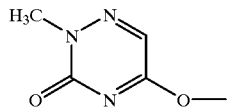

and:
3,5-dioxo-6-amino-(2H,4H)-1,2,4-triazine, (IIIc)

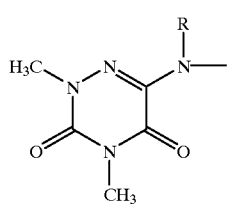

in which R represents a $C_1$–$C_3$ alkyl group, and salts thereof with pharmaceutically-acceptable acids, "cis" and "trans" isomers thereof, and enantiomers of the compounds possessing asymmetric carbons.

2. Compound according to claim 1, characterized in that it is chosen from the following compounds:
cis-2-[4-[4-(3-Chlorophenyl)piperazin-1-yl]-cyclohexyl]-4-methyl-2H-[1,2,4]triazine-3,5-dione fumarate
trans-2-[4-[(2,3-Dihydrobenzo[1,4]dioxin-2-ylmethyl)amino]cyclohexyl]-4-methyl-2H-[1,2,4]triazine-3,5-dione hemifumarate
cis-4-Methyl-2-[4-(4-pyrimidin-2-yl-piperizin-1-yl)cyclohexyl]-2H-[1,2,4]triazine-3,5-dione
trans-4-Methyl-2-[4-(4-pyrimidin-2-yl-piperizin-1-yl)cyclohexyl]-2H-[1,2,4]triazine-3,5-dione
trans-4-Methyl-2-[4-[4-(4,6-dimethylpyrimidin-2-yl)piperizin-1-yl]cyclohexyl]-2H-[1,2,4]triazine-3,5-dione and
trans-4-Methyl-2-[4-[4-(4-methylpyrimidin-2-yl)piperazin-1-yl]cyclohexyl]-2H-[1,2,4]triazine-3,5-dione
trans-2-[4-[4-(4-chloropyrimidin-2-yl)piperazin-1-yl]cyclohexyl]-4-methyl-2H-[1,2,4]triazine-3,5-dione
trans-2-[4-[4-(5-Fluoropyrimidin-2-yl)piperizin-1-yl]cyclohexyl]-4-methyl-2H-[1,2,4]triazine-3,5-dione
trans-2-Methyl-5-[4-(4-pyrimidin-2-yl-piperizin-1-yl)cyclohexyloxy]-2H-[1,2,4]triazin-3-one
trans-2-Methyl-5-[4-[4-(4-methylpyrimidin-2-yl)piperazin-1-yl]cyclohexyloxy]-2H-[1,2,4]triazin-3-one
trans-2-Methyl-5-[4-[4-(4,6-dimethylpyrimidin-2-yl)piperazin-1-yl]cyclohexyloxy]-2H-[1,2,4]triazin-3-one
trans-2-Methyl-5-[4-[4-(4-chloropyrimidin-2-yl)piperazin-1-yl]cyclohexyloxy]-2H-[1,2,4]triazin-3-one
trans-2-Methyl-5-[4-[4-(4-methoxypyrimidin-2-yl)piperazin-1-yl]cyclohexyloxy]-2H-[1,2,4]triazin-3-one
trans-2-Methyl-5-[4-[4-(4-trifluoromethylpyrimidin-2-yl)piperazin-1-yl]cyclohexyloxy]-2H-[1,2,4]triazin-3-one
trans-2-Methyl-5-[4-[4-(5-fluoropyrimidin-2-yl)piperazin-1-yl]cyclohexyloxy]-2H-[1,2,4]triazin-3-one
trans-5-[4-[(2,3-dihydrobenzo[1,4]dioxin-2-ylmethyl)amino]cyclohexyloxy]-2-methyl-2H-[1,2,4]triazin-3-one
trans-6-({4-[4-(3-Chlorophenyl)piperazin-1-yl]cyclohexyl}methylamino)-2,4-dimethyl-2H-[1,2,4]triazine-3,5-dione
cis-6-({4-[4-(3-Chlorophenyl)piperazin-1-yl]cyclohexyl}methylamino)-2,4-dimethyl-2H-[1,2,4]triazine-3,5-dione.

3. Process for the preparation of a chemical compound according to claim 1, characterized in that a derivative of general formula IV

in which A' a compound of represents the IIa or IIb groups described above, is treated with an intermediate of type Va or Vb

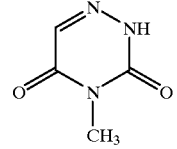

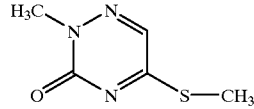

the condensation between the derivatives IV and Va being carried out according to the conditions of the Mitsunobu reaction, and the condensation between the derivatives IV and Vb being carried out in the presence of sodium hydride or of potassium tert-butoxide in dioxane or THF.

4. Pharmaceutical composition, characterized in that it comprises, as active principle, a compound according to claim 1.

5. Pharmaceutical composition, characterized in that it comprises a compound according to either of claim 2 in combination with a pharmaceutically-acceptable excipient.

6. A method for the treatment of depression and anxiety requiring an agonist of 5-$HT_{1A}$ receptors, comprising the step of administering to a living animal suffering from such disorder an amount of a compound of claim 1 effective for alleviation of such disorder.

* * * * *

UNITED STATES PATENT AND TRADEMARK OFFICE
CERTIFICATE OF CORRECTION

PATENT NO. : 6,191,130 B1  
DATED : February 20, 2001  
INVENTOR(S) : JEAN-FRANCOIS PATOISEAU, ELISABETH DUPONT-PASSELANIGUE, WOUTER KOEK It is certified that error appears in the above-identified patent and that said Letters Patent is hereby corrected as shown below:

Column 24, line 20; The word "and" should be placed after --dione--

Column 24, line 33; remove "a compound of " after "A" and replace it after --represents--

Column 24, line 60; delete "either of" after "to"

Signed and Sealed this

Fifth Day of June, 2001

Attest:

Attesting Officer

NICHOLAS P. GODICI  
*Acting Director of the United States Patent and Trademark Office*